US009492153B2

(12) United States Patent
Vaillancourt et al.

(10) Patent No.: US 9,492,153 B2
(45) Date of Patent: Nov. 15, 2016

(54) WOUND PROTECTOR

(71) Applicants:Michael J. Vaillancourt, Chester, NJ (US); Marshall Kerr, Carlsbad, CA (US); Gregory J. Dwyer, Wayne, NJ (US); Jeicol Herrera, Morristown, NJ (US); Michael J. Pfefferkorn, Randolph, NJ (US)

(72) Inventors: Michael J. Vaillancourt, Chester, NJ (US); Marshall Kerr, Carlsbad, CA (US); Gregory J. Dwyer, Wayne, NJ (US); Jeicol Herrera, Morristown, NJ (US); Michael J. Pfefferkorn, Randolph, NJ (US)

(73) Assignee: VLV Associates, Inc., Whippany, NJ (US)

( * ) Notice: Subject to any disclaimer, the term of this patent is extended or adjusted under 35 U.S.C. 154(b) by 0 days.

(21) Appl. No.: 14/523,157

(22) Filed: Oct. 24, 2014

(65) Prior Publication Data

US 2015/0119647 A1 Apr. 30, 2015

Related U.S. Application Data

(60) Provisional application No. 61/895,727, filed on Oct. 25, 2013.

(51) Int. Cl.
*A61B 1/32* (2006.01)
*A61B 17/02* (2006.01)
*A61B 17/34* (2006.01)
*A61B 17/00* (2006.01)

(52) U.S. Cl.
CPC ........ *A61B 17/0293* (2013.01); *A61B 17/3423* (2013.01); *A61B 2017/00407* (2013.01); *A61B 2017/00991* (2013.01)

(58) Field of Classification Search
CPC .......... A61B 17/3423; A61B 17/3431; A61B 17/0293; A61B 17/0281; A61B 2017/3435; A61B 2017/0225
See application file for complete search history.

(56) References Cited

U.S. PATENT DOCUMENTS

| 4,188,945 | A | * | 2/1980 | Wenander | A61B 19/08 128/850 |
|---|---|---|---|---|---|
| 5,640,977 | A | * | 6/1997 | Leahy | A61B 17/3423 128/850 |
| 6,142,935 | A | * | 11/2000 | Flom | A61B 17/0293 600/206 |
| 6,254,534 | B1 | * | 7/2001 | Butler | A61B 1/32 600/206 |
| 7,537,564 | B2 | * | 5/2009 | Bonadio | A61B 17/0293 600/208 |
| 8,734,336 | B2 | * | 5/2014 | Bonadio | A61B 17/0293 600/203 |
| 2004/0049099 | A1 | * | 3/2004 | Ewers | A61B 1/32 600/206 |

(Continued)

*Primary Examiner* — Jacqueline Johanas
(74) *Attorney, Agent, or Firm* — Francis C. Hand; Carella, Byrne, et al.

(57) ABSTRACT

In one embodiment, the wound protector has an annularly collapsible proximal ring and a flexible sleeve extends between the proximal ring and distal ring. After positioning of the distal ring in a wound, the proximal ring is expanded to draw the sleeve taut between the rings 11, 12 and is drawn tight against the wound.

In a second embodiment, the wound protector has a flexible sleeve secured between a distal ring and proximal ring of fixed diameters. In addition, an expansion member is disposed within a loop of the flexible sleeve about the proximal ring. After positioning of the distal ring in a wound, movement of the expansion member into an extended diametric state expands the loop in the sleeve diametrically while drawing the rings towards each other.

3 Claims, 9 Drawing Sheets

(56) References Cited

U.S. PATENT DOCUMENTS

| | | | |
|---|---|---|---|
| 2004/0054353 A1* | 3/2004 | Taylor | A61B 17/3423 606/1 |
| 2005/0020884 A1* | 1/2005 | Hart | A61B 17/0293 600/206 |
| 2005/0090717 A1* | 4/2005 | Bonadio | A61B 17/0293 600/208 |
| 2005/0192483 A1* | 9/2005 | Bonadio | A61B 17/3423 600/208 |
| 2006/0149306 A1* | 7/2006 | Hart | A61B 17/3423 606/191 |
| 2006/0247498 A1* | 11/2006 | Bonadio | A61M 13/003 600/208 |
| 2007/0225569 A1* | 9/2007 | Ewers | A61B 1/32 600/206 |
| 2008/0200767 A1* | 8/2008 | Ewers | A61B 1/32 600/208 |
| 2010/0063362 A1* | 3/2010 | Bonadio | A61B 17/0293 600/203 |
| 2011/0054260 A1* | 3/2011 | Albrecht | A61B 17/0218 600/208 |
| 2011/0201893 A1* | 8/2011 | O'Prey | A61B 17/3423 600/208 |
| 2011/0282157 A1* | 11/2011 | Hart | A61B 17/0293 600/208 |
| 2012/0245427 A1* | 9/2012 | Kleyman | A61B 17/0293 600/208 |
| 2013/0066156 A1* | 3/2013 | Seo | A61B 17/3423 600/204 |
| 2013/0184535 A1* | 7/2013 | Suh | A61B 17/0293 600/210 |
| 2013/0217973 A1* | 8/2013 | Ewers | A61B 1/32 600/203 |
| 2014/0142392 A1* | 5/2014 | Smith | A61B 17/3423 600/203 |
| 2014/0316210 A1* | 10/2014 | Koehler | A61M 3/02 600/208 |

* cited by examiner

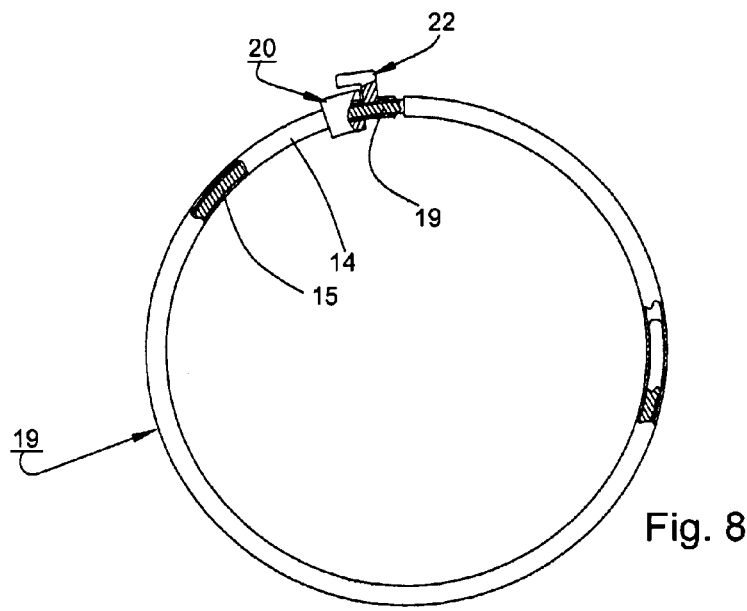
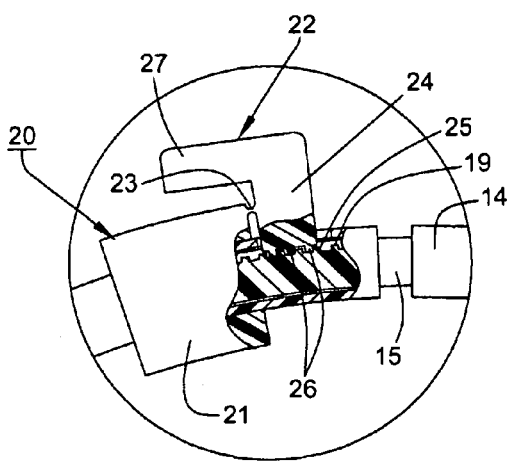
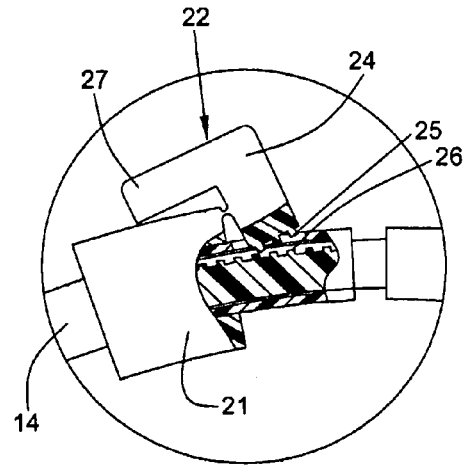
Fig. 8
Fig. 9
Fig. 10

WOUND PROTECTOR

This application claims the benefit of Provisional Patent Application 61/895,727, filed Oct. 25, 2013.

This invention relates to a wound protector.

As is known, wound protectors of a type as described in U.S. Pat. No. 8,231,527 are used, in particular, to provide access to internal tissue through open surgical procedures and endoscopic surgical procedures. As described, the wound protector is formed of a pair of rings with a flexible sleeve secured between the two rings. When used, the wound protector in positioned in a patient's abdominal wall through an incision. The distal ring is held in a collapsed position and then inserted through the incision (46). After insertion, the distal ring is released and then expands to its ring-like shape. The proximal ring is rollable to gather the flexible sleeve around the proximal ring and the wound proximal ring sits on the cutaneous surface of the abdominal wall. Shortening of the sleeve pulls the sleeve taut against the incised wound.

Rolling of the proximal ring of the known wound protectors can be cumbersome for a user, particularly where the ring is to rest against the patient.

Accordingly, it is an object of the invention to provide a wound protector that can positioned in a patient by a single practitioner.

It is another object of the invention to provide a wound protector that can be efficiently put in place in a patient.

It is another object of the invention to provide a wound protector that can be readily manipulated to achieve a secure position within an incision in a patient.

Briefly, in one embodiment, the invention provides a wound protector comprised of a collapsible distal ring, an annularly collapsible proximal ring and a flexible sleeve extending between the proximal ring and the distal ring.

In accordance with the invention, the proximal ring is circumferentially collapsible from an extended state wherein the diameter of the proximal ring is larger than the diameter of the distal ring to a collapsed state wherein the diameter of the proximal ring is of the same size as the diameter of the distal ring.

The flexible sleeve forms a frusto-conical shape with the proximal ring in the extended state and collapses with the proximal ring when the proximal ring is moved into the collapsed state.

In use, the wound protector may be deployed, for example, as described in U.S. Pat. No. 8,231,527 in a patient's abdominal wall through an incision. In this case, the distal ring is held in a collapsed position to reduce its size and then inserted through the incision. After insertion, the distal ring is released to allow the ring to expand to a ring shape and to seat against the peritoneal surface of the abdominal wall.

During insertion of the distal ring into a patient, the proximal ring is manually squeezed to annularly collapse from the extended state to the collapsed state. This allows the flexible sleeve between the rings to become slack between the rings and to move through the incision.

After the distal ring is positioned within the patient, the proximal ring is released to expand into the extended state and to lie against the abdomen of the patient. At this time, the otherwise slack flexible sleeve is drawn tight against the wound made by the incision.

In another embodiment, the wound protector comprises a collapsible distal ring; a proximal ring; a flexible sleeve extending between the two rings and disposed within and over the proximal ring to form a loop thereover; and an expansion member disposed within the loop of the flexible sleeve for movement between a collapsed diametric state and an extended diametric state. Movement of the expansion member into the extended diametric state expands the loop diametrically while drawing the distal ring and the proximal ring towards each other.

In still another embodiment, the wound protector comprises a collapsible distal ring; a proximal ring; a sleeve having a first annular section secured to said distal ring, a second annular section peripherally secured to said first annular section and a third annular section peripherally secured to said second annular section and an expansion member disposed with the loop of the flexible sleeve for movement between a collapsed diametric state and an extended diametric state, wherein movement of the expansion member into the extended diametric state expands the loop diametrically while drawing the distal ring and the proximal ring towards each other.

In still another embodiment, the wound protector comprises a collapsible distal ring; a flexible sleeve extending from said distal ring and having a loop at one end thereof; and an expansion member disposed within the loop of the flexible sleeve for movement between a collapsed diametric state and an extended diametric state, wherein movement of the expansion member into the extended diametric state expands the loop diametrically while drawing the distal ring and the expansion member towards each other.

These and other objects and advantages of the invention will become more apparent from the following detailed description taken in conjunction with the accompanying drawings wherein:

FIG. 8 illustrates a top view of a modified distal ring in accordance with the invention;

FIG. 9 illustrates a view of a finger grip in a locking position for locking the distal ring of FIG. 8 against collapsing;

FIG. 10 illustrates a view similar to FIG. 9 with the finger grip in a release position to allow expansion or contraction of the distal ring;

Figure 1:
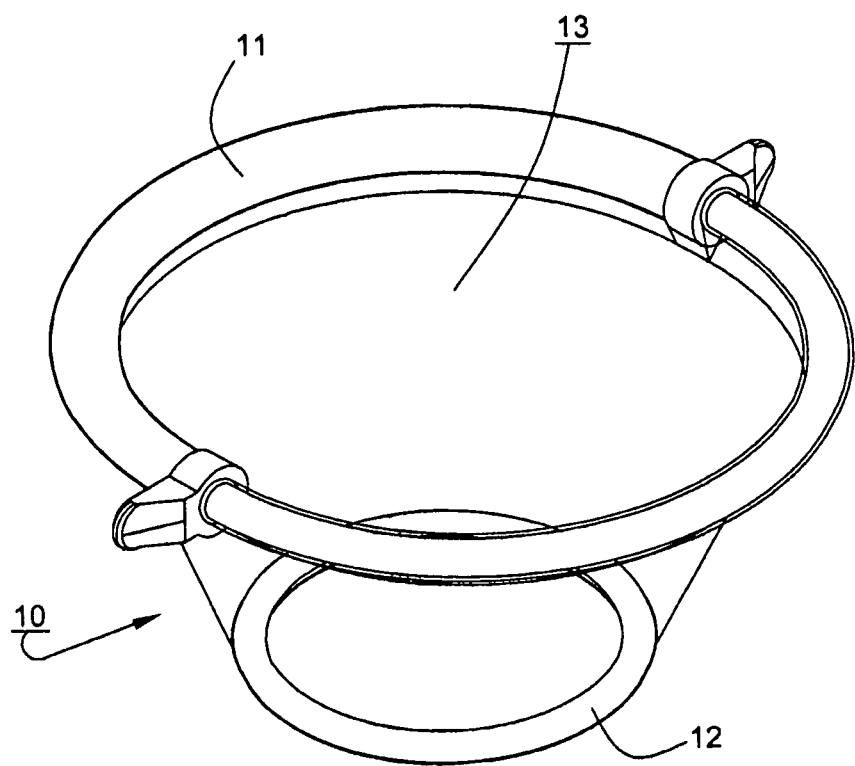
FIG. 1 depicts a perspective view of a wound protector of the invention in an extended state.

Referring to FIG. 1, the wound protector 10 comprises an annularly collapsible proximal ring 11, a distal ring 12 and a flexible sleeve 13 having a length extending between the proximal and distal rings 11, 12.

Figure 2:
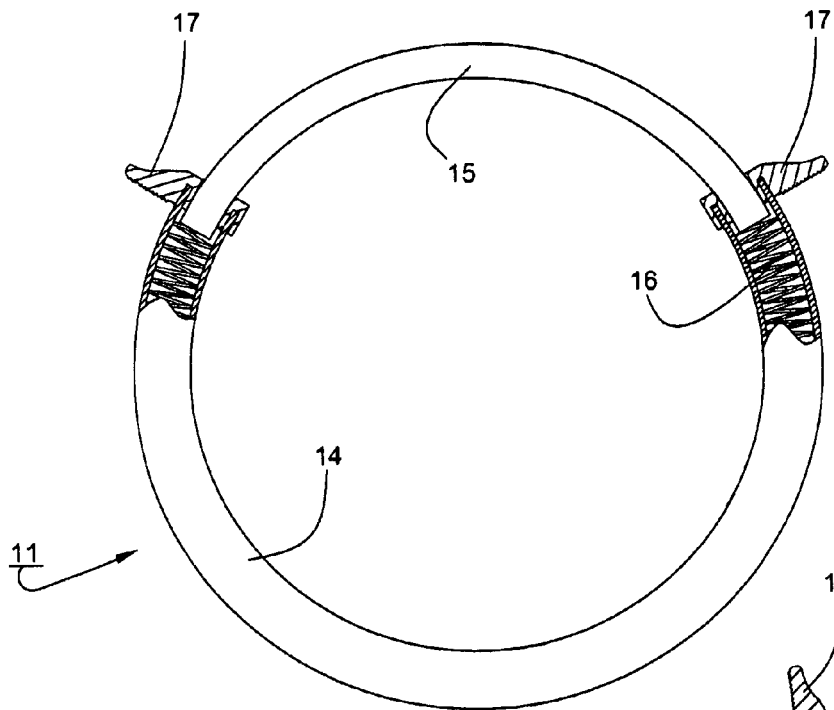
FIG. 2 illustrates a top view of the distal ring of the wound protector of FIG. 1 in an extended state.
Figure 3:
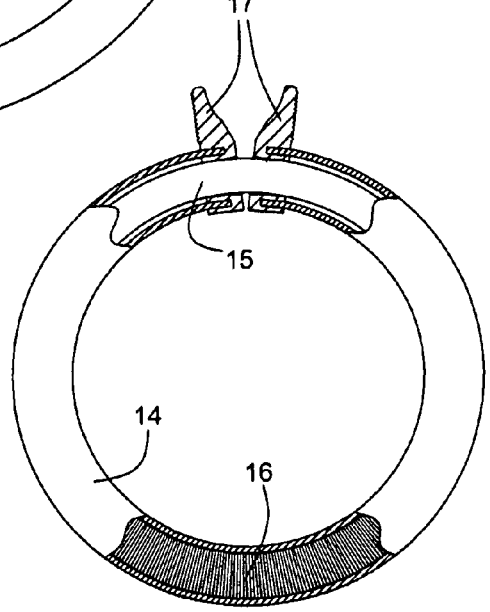
FIG. 3 illustrates a top view of the distal ring of the wound protector of FIG. 1 in a collapsed state.

Referring to FIGS. 2 and 3, the proximal ring 11 is formed of a one-piece hollow tube 14 bent into an open-ended annular shape, an arcuate rod 15 slidably disposed within the tube 14 to bridge the open end of the tube 14 and a compression spring 16 located within the tube 14 and butted against the ends of the rod 15 (see FIG. 3). In addition, each end of the tube 14 carries a finger grip 17 which is secured to the end of the tube 14 in any suitable manner, such as by gluing.

The tube 14 is made of any suitable material, such as a plastic, e.g. Delrin (Polyoxymethylene) or Teflon (polytetrafluoroethylene) that permits the tube 14 to be bent, i.e. to be circumferentially collapsed on itself. Likewise, the rod 15 is made of a suitable material to be bent so as to follow the contour of the tube 14.

The spring 16 may be made of any suitable material, such as a metal.

The finger grips 17 are made of any suitable material, such as a plastic. As illustrated, each finger grip 17 is fitted onto an end of the tube 14 and is fixed thereon by heat sealing, gluing, or the like.

Manual squeezing of the finger grips 17 towards each other causes the ends of the tube 14 to come together as indicated in FIG. 3 while sliding over the rod 15 and compressing the spring 16 within the tube 14. This causes the proximal ring 11 to circumferentially collapse from the expanded state of FIG. 2 to the collapsed state of FIG. 3.

Upon release of the finger grips 17, the spring 16 expands thereby causing the ends of the tube 14 to slide relative to the rod 15 and to bring the tube 14 back into its expended state (FIG. 2).

The distal ring 12 is made of any suitable material, such as urethane, and is of solid cross-section while being of fixed diameter. The distal ring 12 is resiliently flexible in order to be inserted into an incision in a patient in the usual manner.

Figures 6, 7:
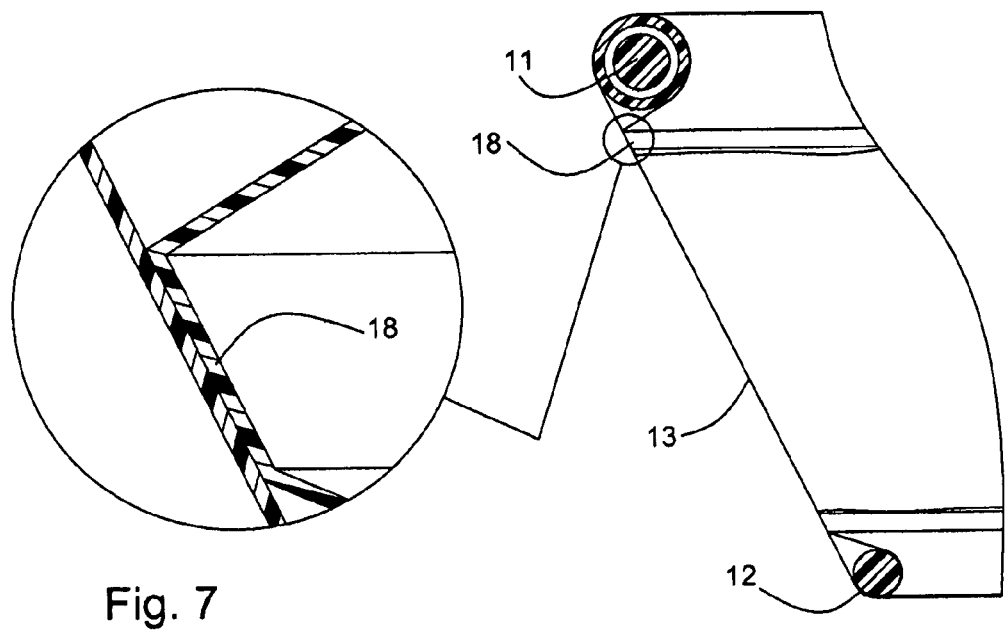
FIG. 6 illustrates a partial view of the flexible sleeve as secured to the proximal ring and disposed about the distal ring.
FIG. 7 illustrates a cross-sectional view of the manner of securing the flexible sleeve about the distal ring.

Referring to FIGS. 6 and 7, the flexible sleeve 13 is made from a sheet of material, such as a urethane film, that is looped at the upper end, as viewed, to envelop the proximal ring 11, overlaid on itself along a longitudinal seam 18 and secured as by welding to the distal ring 12. Since the rings 11, 12 are of different diameters in the expanded state of the proximal ring 11, the sleeve 13 takes on a frusto-conical shape as viewed in FIGS. 1 and 5.

Figure 5:
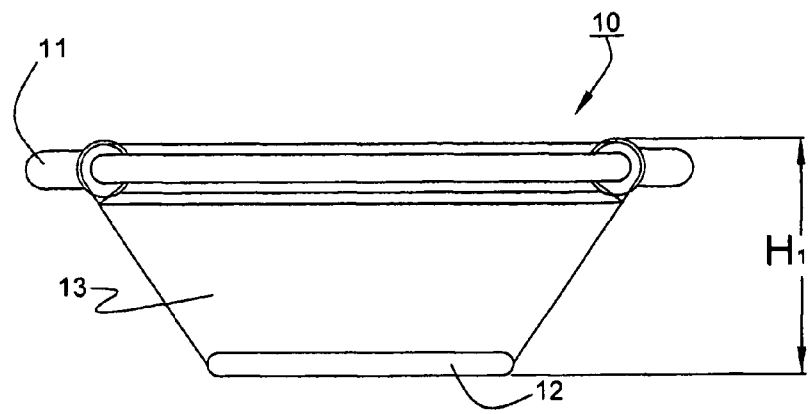
FIG. 5 illustrates a side view of the wound protector of FIG. 1 with the distal ring in the extended state of FIGS. 1 and 2.

As indicated in FIG. 5, the sleeve 13 envelops the finger grips 17 (not shown). As the sleeve 13 is made of urethane film or the like, the sleeve 13 does not become punctured by the finger grips 17 when the finger grips 17 are employed to collapse the proximal ring 11. Also, as the proximal ring 11 is collapsed, the loop formed by the sleeve 11 about the proximal ring 11 collapses in an accordion-like manner to accommodate the collapsing of the proximal ring 11. As the proximal ring 11 returns to the expanded state, the loop formed by the sleeve 11 likewise expands.

During use of the wound protector 10, when the proximal ring 11 is collapsed from the expanded state into the collapsed state (FIG. 4) by manual engagement and squeezing of the finger grips 17 together, the sleeve 13 is able to collapse inwardly as the distal ring 12 is inserted into an incised wound of a patient while the loop formed by the sleeve 13 about the proximal ring 11 collapses.

After placement of the distal ring 12 within the patient, the finger grips 17 are released so that the proximal ring 11 is allowed to expand under the force of the spring 16. As the proximal ring 11 expands, the sleeve 13 expands outwardly while the loop formed by the sleeve 13 about the proximal ring 11 expands in like manner. During this time, the sleeve 13 becomes taut between the rings 11, 12 and is drawn tight against the wound made by the incision.

Figure 4:
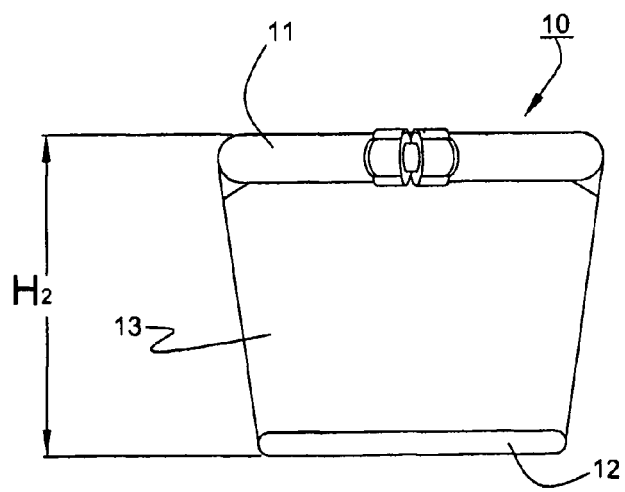
FIG. 4 illustrates a side view of the wound protector of FIG. 1 with the distal ring in the collapsed state of FIG. 3.

Referring to FIGS. 4 and 5, the height of the wound protector 10 from the top of the proximal ring 11 to the bottom of the distal ring is related to the outside diameter OD of the proximal ring 11 such that the height increases from a value of $H_1$ to a higher value of $H_2$ (i.e. the distance between the rings 11,12 increases) as the proximal ring 11 is collapsed (as the OD decreases). That is, the sleeve 13 collapses inwardly on itself while elongating in length. Thus, when the proximal ring 11 expands after implanting of the distal ring 12, the sleeve 13 decreases in length and becomes taut.

Referring to FIG. 8, wherein like reference characters indicate like parts as above, the proximal ring 19 may also be formed from a tube 14 as above with an internal rod 15' that is provided with serrations 19 at least along a length that is adjacent the ends of the tube 14. A spring (not shown) as in the embodiment of FIGS. 1 to 7 may be employed to provide for an automatic spring back of the proximal ring 19 to an expanded state in a manner as described above. Alternatively, a spring may be omitted within the tube 14 and between the ends of the rod 15' so that a manual force is required to return the proximal ring 19 to the expanded state.

In addition, a single finger grip 20 is mounted on one end of the tube 14 for locking the tube 14 relative to the rod 15'. As illustrated, the finger grip 20 has a body 21 concentrically mounted on the tube 14 in a fixed manner and a detent 22 that is integrally connected to the body 21 via a flexure 23. As indicated, the finger grip 20 is made in one piece.

The detent 22 is of L-shape with one leg 24 that projects through a slot 25 in the tube 14 and that has a plurality of teeth 26, e.g. three teeth, at one end engaging with the serrations 19 of the rod 15' in order to lock the tube 14 relative to the rod 15'. A second leg 27 of the detent 22 extends longitudinally of the tube 14 and over the body 21 so as to be manually pivotable via the flexure 23 relative to the body 21 and the tube 14 between a lowered position as shown in FIG. 9 and a raised position as shown in FIG. 10.

With the detent 22 in the lowered position of FIG. 9, the leg 24 engages with the rod 15' to prevent relative movement between the tube 14 and rod 15'.

With the detent 22 in the raised position of FIG. 10, the leg 24 is spaced from the rod 15' to allow relative movement between the tube 14 and rod 15'. When the detent is in the raised position, the tube 14 may be manually collapsed or, where a spring is present as above described, the tube 14 automatically expands to its expanded state.

The detent 22 allows for the proximal ring 19 to be adjusted in circumference to any point between the fully collapsed state and the fully expanded state by selectively engaging the teeth 26 of the detent 22 with the serrations in the rod 15'.

The proximal ring 19 of FIGS. 8 to 10 functions in the same manner as the proximal ring 11 of FIGS. 1 to 6 and is enveloped by a sleeve as above described.

In use, when a wound protector employing the proximal ring 19 (not shown) is to be placed through an incision and into a patient, the detent 22 is manually pivoted, e.g. by a user's thumb, into the unlocked position of FIG. 10 to allow the user to manually circumferentially collapse the proximal ring 19 to a desired size. The detent 22 is then released to allow the detent 22 to re-engage the rod 15' in a locked position as shown in FIG. 9 and the distal ring (not shown) be placed through the incision.

After placement of the distal ring (not shown) in the patient, the detent 22 is again pivoted into the unlocked position to allow the proximal ring 19 to be expanded circumferentially by a manual force thereby pulling the sleeve between the rings taut.

Figure 11:
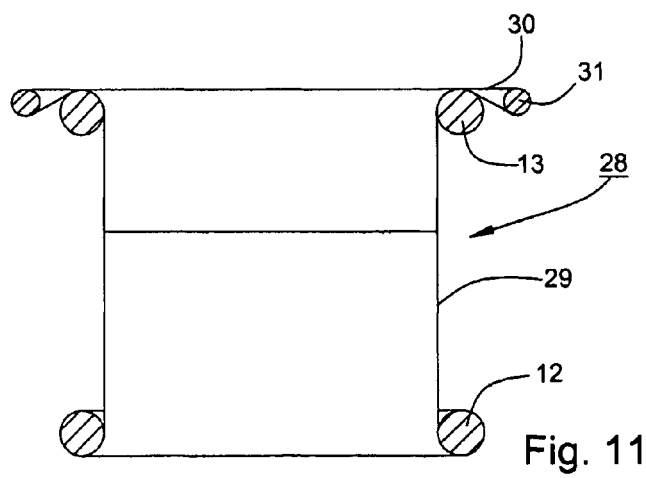
FIG. 11 illustrates a schematic view of a wound protector in accordance with a second embodiment of the invention with an expansion member in a collapsed diametric state.

Referring to FIG. 11, wherein like reference characters indicate like parts as above, the wound protector 28 comprises a collapsible distal ring 12, a proximal ring 13 of equal diameter to the distal ring 12 and a flexible sleeve 29 that extends between the distal ring 12 and the proximal ring 13 with the sleeve 29 being disposed within and over the proximal ring 13 to form a loop 30 thereover.

In addition, the wound protector 28 includes an expansion member 31 that is disposed within the loop 30 formed by the flexible sleeve 29 or movement between a collapsed diametric state (FIG. 11) and an extended diametric state (FIG. 13) so that movement of the expansion member 31 into the extended diametric state expands the loop 30 diametrically while drawing the rings 12, 13 towards each other.

Figure 14:
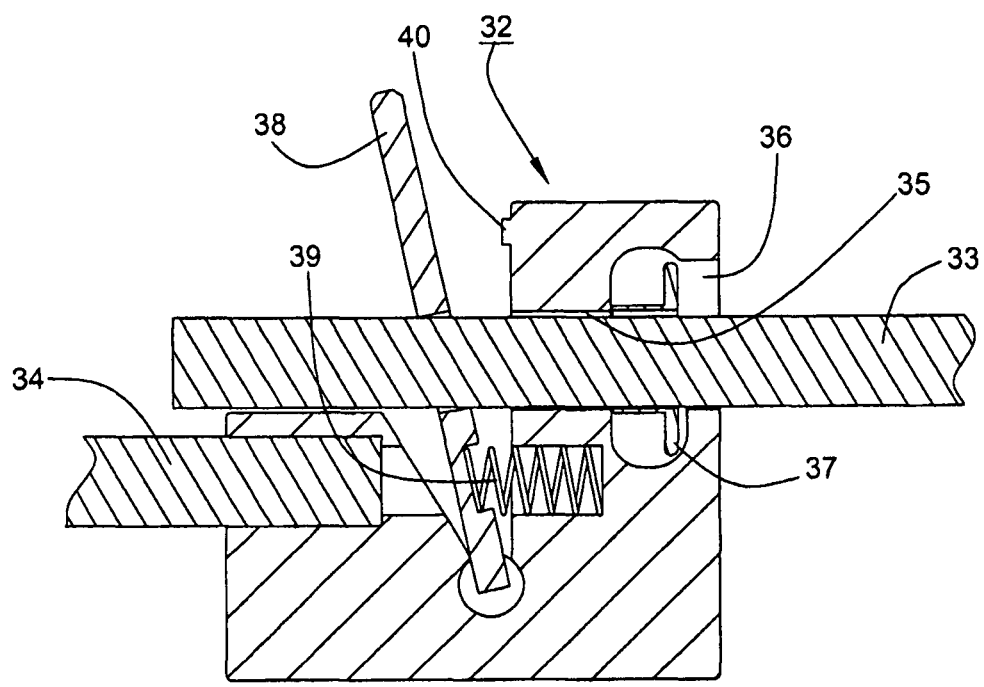
FIG. 14 illustrates a cross-sectional side view of a locking device employed in the wound protector of FIG. 11.

Referring to FIG. 14, the expansion member 31 includes a locking device 32 and a rod 33. The rod 33 has one end 34 secured in a bore of the locking device 32, an intermediate section extending circumferentially within the loop 30 and passing through the locking device 32 and a second end (not shown) extending outwardly from the locking device 32 and the loop 30 for manual gripping thereof.

The loop 30 of the flexible sleeve 29 includes an opening (not shown) for passage of the expansion member 31 therethrough that extends longitudinally of the sleeve 29 for a short distance sufficient to allow the expansion member 31 to be inserted into the loop 30. A rod (not shown) may be made integral with the sleeve 29 to extend along the opening in order to reinforce a side of the opening.

In addition, the rod (not shown) may be welded in place not only along the length thereof to the sleeve 29 to form a reinforced welting but also at one end to the proximal ring 13.

Referring to FIG. 14, the locking device 32 has a block-like shape with a bore on one side to receive the end 34 of the rod 33 in fixed manner and a through bore 35 in an upstanding portion through which the intermediate section of the rod 33 passes. The locking device 32 also includes a transversely disposed slot 36 in the upstanding portion that receives a roller 37 that is rotatably mounted coaxially in a loose manner on the rod 33 within the slot 36. That is, the rod 33 is allowed to move longitudinally within the roller 37 while the roller 37 is free to rotate on the rod 33.

The rod (not shown) that is welded to the sleeve 29 is received in the slot 36 and rests on the roller 37.

During expansion and retraction of the wound protector 28, the locking device 32 remains anchored to the rod 33 and sleeve 29 while the rod 33 is allowed to move transversely as the roller 37 rotates.

The locking device 32 includes a lever 38 with a bore through which the rod 33 passes. This lever 38 is movable between a locking position securing the projecting end of the rod 33 from movement away from the locking device 32 and a release position allowing movement of the end free of the rod 33 into and from the locking device 32. As indicated, the lever 38, in a conventional manner, is freely mounted in the locking device 32 and is biased by a spring 39 into the locking position.

A stop 40 is also provided on the locking device 32 to prevent the lever 38 to passing beyond a dead-center position as is conventional.

A flap (not shown) of the same material as the sleeve 29 is secured to the sleeve 29 to cover the opening for the expansion member 31.

Figure 15:
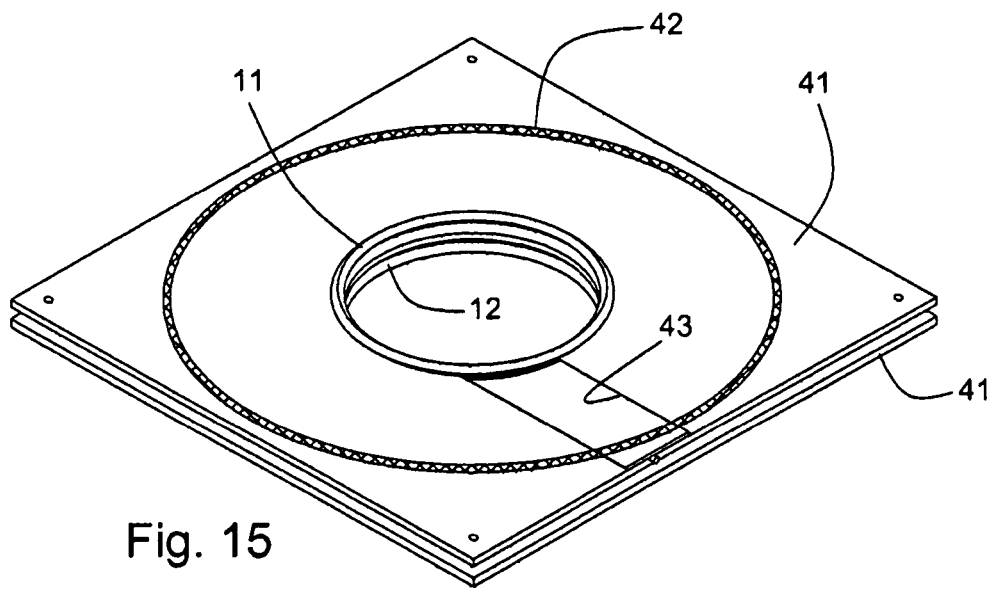
FIG. 15 illustrates a step in the process of fabrication of the wound protector of FIG. 11.

Referring to FIG. 15, during assemblage of the wound protector 28, each ring 11, 12 is separately welded to a sheet of urethane film 41. Thereafter, the two resulting units are placed on top of each other, the film material within the rings 11, 12 is removed, a circular cut is made in the sheets concentric to the rings 11, 12 and the peripheral annular edges 42 of the two sheets of film are welded to each other to form the sleeve 29.

Prior to the above steps, the upper sheet of film, as viewed, is cut to form a gap 43, a rod (not shown) is welded along one edge of the gap 41 and the flap (not shown) is welded over the gap 43.

Thereafter, the proximal ring 13 is rolled over on itself in order to be covered by the sleeve 29 and to form the loop 30 and the expansion member 31 inserted through the gap 41

In order to fit the locking device 32 in place, with the roller 37 in the slot 36 and the rod 33 disposed across the roller 37, the end of the rod 33 that is to be secured in the locking device 32 is slid through the lever 38, the through bore 35 and over the roller 37 thereby anchoring the locking device 32 to the rod 33 and sleeve 29. The end 34 of the rod 33 is then threaded through the loop 30 and inserted in the bore of the locking device 32 and fixed in place, e.g. by means of a glue. The trailing end of the rod 33 remains outside the loop 30 for manual grasping by the ultimate user.

The trailing end of the rod 33 may be provided with a gripping surface (not shown), such as a rubber sleeve, to facilitate movement of the rod 33 when in use In use, the distal ring 12 is inserted manually through an incision in a patient with the use of one hand of the practitioner with the proximal ring 11 resting against the body of the patient (not shown) outside the incision.

Figure 13:
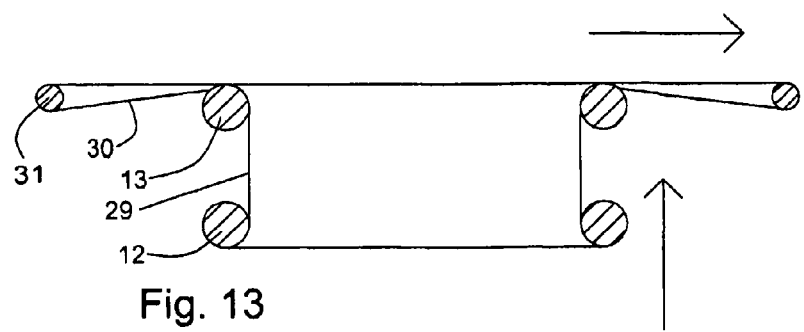
FIG. 13 illustrates a schematic cross-sectional view of the wound protector of FIG. 16 with the expansion member in a fully extended diametric state position.
Figure 12:
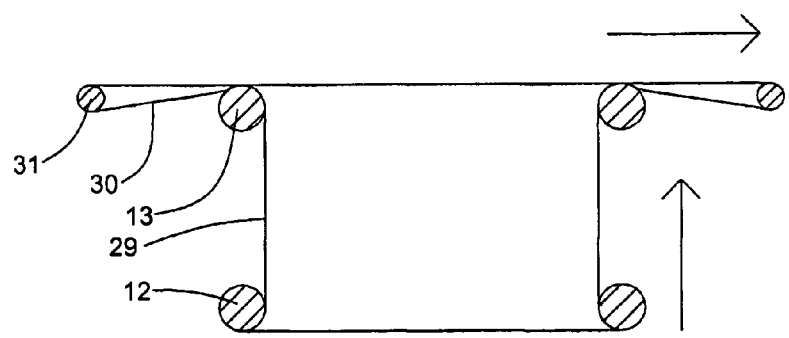
FIG. 12 illustrates a schematic side view of the wound protector of FIG. 11 with the expansion member in a partially extended diametric state.

Once the distal ring 12 is in place, the expansion member 31 is manipulated by the practitioner to expand circumferentially from the collapsed state shown in FIG. 11 through the partially expanded state shown in FIG. 12 to the fully expanded state shown in FIG. 13. During this time, the distal ring 12 is drawn upwardly, as viewed, and as indicated by the arrows while the expansion member 31 expands radially outwardly as indicated by the arrows. The sleeve 29 is thus moved to the extended diametric state while being held taut between the rings 12, 13.

Figure 16:
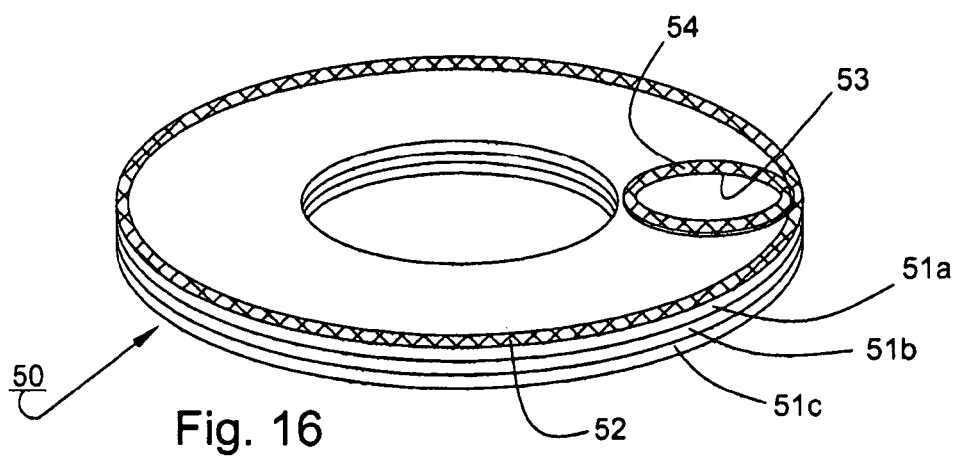
FIG. 16 illustrates a perspective view of a retractor assembly for forming a wound protector in accordance with a third embodiment of the invention.

Referring to FIG. 16, wherein like reference characters indicate like parts as above, in another embodiment of the wound protector, a retractor assembly 50 is provided to form a sleeve for securement to a distal ring (not shown) and a proximal ring (not shown).

As illustrated, the retractor assembly 50 has three annular sections 51a, 51b, 51c, each of urethane film, that are welded together to form a unitary joint or seam 52 at the outer periphery. The uppermost annular section 51a is provided with an opening 53 with a reinforced inner edge 54.

After forming the retractor assembly 50, the inner peripheral edge of the uppermost annular section 51a is folded about the unitary joint 52 and welded to a first or proximal ring (not shown). Next, the middle annular section 51b is folded about the unitary joint 52 and the inner peripheral edge the remaining lowermost annular section 51c is welded to the proximal ring at about a diametrically opposite point. Thus, the two annular sections 51a, 51c form a closed pocket with the proximal ring but for the opening 53 which opens into the pocket.

Next, the inner peripheral edge of the middle annular section 51b is welded to a second or distal ring.

Thereafter, the distal ring is rolled 360° to roll the inner periphery of the middle annular section 51b to the inside of the ring such that the ring is located to the outside of the annular section 51b.

Likewise, the proximal ring is rolled 360° to roll the inner peripheries of the upper and lower annular sections 51a, 51c to the inside of the ring along with the pocket therebetween such that the ring is enveloped by the two sections 51a, 51c.

Next, an expansion member 31, as described above, is inserted through the opening 53 to be located at the outer side of the proximal ring.

When in use in a patient, after the distal ring has been inserted in a patient, expansion of the expansion member 31 draws the pocket formed by annular sections 51a, 51c from within the confines of the distal ring and radially outwardly of the proximal ring while the distal ring and proximal ring are drawn towards each other in a manner similar to that illustrated by FIGS. 11 to 13.

In still another embodiment (not shown), the wound protector includes a collapsible distal ring, a flexible sleeve extending from the distal ring and having a loop at one end thereof and an expansion member disposed within the loop for movement between a collapsed diametric state and an extended diametric state. Movement of the expansion member into the extended diametric state expands the loop diametrically while drawing the distal ring and the expansion member towards each other. In this embodiment, the expansion member doubles as the expansion member and a proximal ring.

Figure 17:
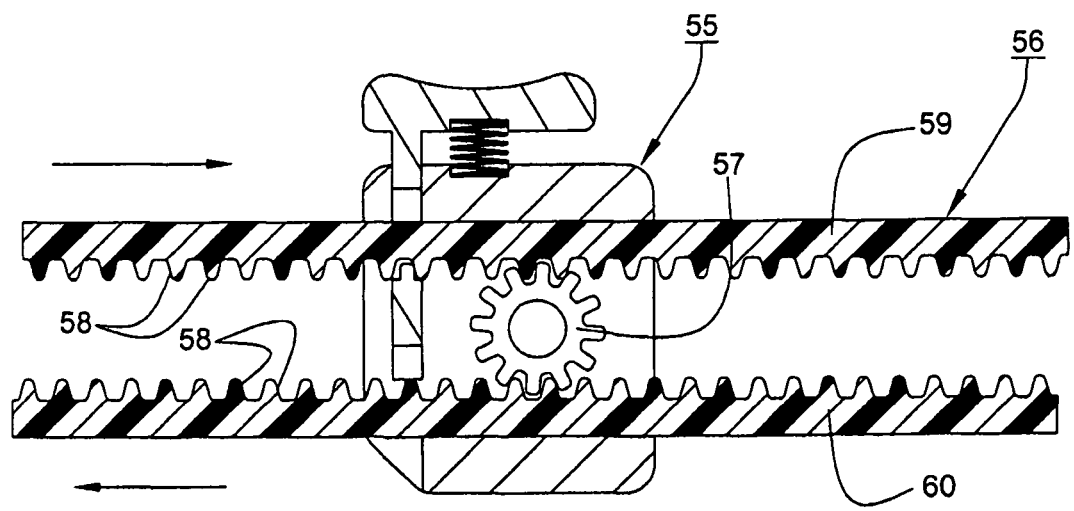
FIG. 17 illustrates a cross-sectional view of a modified locking device in accordance with the invention.

Referring to FIG. 17, the expansion member of the invention may be modified to have a locking device 55 and a rod 56 wherein the locking device 55 includes a rotatably mounted gear 57 and the rod 56 has a plurality of serrations 58. In addition, the rod 56 has a first section 59 passing through the locking device with the serrations 58 thereof in meshing engagement with one side of the gear 57 and a second section 60 passing through the locking device 55 with the serrations 58 thereof in meshing engagement with an opposite side of the gear 57 whereby rotation of the gear 57 moves the two sections 59, 60 in opposite directions. Thus, when the expansion member is to be expanded, the free end (not shown) of the rod 56 is grasped manually and pushed into the locking device causing the two sections 59, 60 to move in opposite directions.

The locking device 55 includes a detent for movement between a locking position engaging between serrations of one of the two sections 59, 60 to prevent movement of the two sections and a release position spaced therefrom to allow movement of the two sections.

The invention thus provides a wound protector that can positioned in a patient by a single practitioner. In addition, the wound protector that can be efficiently put in place in a patient and readily manipulated to achieve a secure position within an incision in a patient.

The wound protector does not require a user to roll a proximal ring outside of an incision in order to draw the ring against a patient.

The wound protector may be manipulated by a single user in order to be placed within an incision of a patient.

What is claimed is:

1. A wound protector comprising
a collapsible distal ring;
a proximal ring;
a flexible sleeve extending between said proximal ring and said distal ring, said sleeve being disposed within and over said proximal ring to form a loop thereover; and
an expansion member disposed within said loop of said flexible sleeve for movement between a collapsed diametric state and an extended diametric state, wherein movement of said expansion member into said extended diametric state expands said loop diametrically while drawing said distal ring and said proximal ring towards each other,
said expansion member including a locking device and a first rod, said rod having one end secured in said locking device, an intermediate section extending circumferentially within said loop and passing through said locking device and a second end extending outwardly from said locking device and said loop for manual gripping thereof.

2. A wound protector as set forth in claim 1 wherein said locking device includes a transversely disposed slot and wherein a roller is mounted coaxially on said first rod within said slot of said locking device.

3. A wound protector as set forth in claim 1 wherein said locking device includes a lever having said first rod passing therethrough, said lever being movable between a locking position securing said second end of said first rod from movement away from said locking device and a release position allowing movement of said second end of said first rod from said locking device.

* * * * *